US005287749A

United States Patent [19]

Nakamura

[11] Patent Number: 5,287,749

[45] Date of Patent: Feb. 22, 1994

[54] THERMOMECHANICAL ANALYZER

[75] Inventor: Nobutaka Nakamura, Tokyo, Japan

[73] Assignee: Seiko Instruments, Inc., Tokyo, Japan

[21] Appl. No.: 774,092

[22] Filed: Oct. 11, 1991

[30] Foreign Application Priority Data

Oct. 11, 1990 [JP] Japan ................................ 2-272818

[51] Int. Cl.[5] ........................................ G01N 3/32

[52] U.S. Cl. ........................................ 73/808

[58] Field of Search ................................ 73/789–791, 73/806–808, 811–817

[56] References Cited

U.S. PATENT DOCUMENTS

| | | | |
|---|---|---|---|
| 3,699,808 | 10/1972 | Ford et al. | 73/789 |
| 3,948,091 | 4/1976 | Voll | 73/806 |
| 3,969,930 | 7/1976 | Prevorsek et al. | 73/789 |
| 4,794,788 | 1/1989 | Masters et al. | 73/841 |
| 4,967,601 | 11/1990 | Teramoto | 73/789 |
| 5,079,955 | 1/1992 | Eberhardt | 73/812 |

OTHER PUBLICATIONS

Wen et al., "Measurement of Dynamic Viscoelastic Properties of Corn Horny Endosperm", J. of Materials, vol. 5, No. 4, Dec. 1970.

*Primary Examiner*—Robert Raevis

*Attorney, Agent, or Firm*—Spensley, Horn, Jubas & Lubitz

[57] ABSTRACT

A thermomechanical analyzer for efficiently measuring the dynamic viscoelasticity of a sample piece. The analyzer is provided with a function generator, a stress applier, a strain detector, an analog-to-digital converter, a memory and a Fourier transform processor. The function generator generates a sine wave signal to induce a sine wave stress-strain response in the sample piece. This response is Fourier-transformed by the processor to calculate the dynamic viscoelasticity of the sample piece.

2 Claims, 3 Drawing Sheets

THERMOMECHANICAL ANALYZER

BACKGROUND OF THE INVENTION

The present invention relates to a thermomechanical analyzer for measuring mechanical characteristics of materials as a function of temperature and time.

Conventionally, in such type of analyzer, the dynamic viscoelasticity of a sample piece is measured by directly detecting and analyzing the amplitude ratio and phase difference between a stress signal and a strain signal. In another method, the dynamic viscoelasticity is measured by reading a Lissajous pattern indicated on a stress-strain coordinate plane.

Prior art devices of this type exhibit various drawbacks, such as complicated and troublesome processing for obtaining a measured value of dynamic viscoelasticity. For example, it is difficult to accurately detect the phase difference between the stress signal and the strain signal in the first-mentioned conventional device. With regard to the second conventional device, geometrical computation is needed during each period for reading of the Lissajous pattern.

SUMMARY OF THE INVENTION

An object of the present invention is to eliminate the above noted drawbacks of the prior art.

The above and other objects are achieved, according to the present invention, by a thermomechanical analyzer composed of a function generator for generating a sine wave signal having a desired frequency, a stress applier connected to the function generator for applying a sine wave stress to a sample piece, a strain detector for detecting a sine wave strain induced in the sample by the sine wave stress, an analog digital converter for effecting analog-to-digital conversion of outputs from the stress applier and the strain detector, a memory for storing outputs from the analog digital converter, and a processor for carrying out Fourier transform of data from the memory to calculate the dynamic viscoelasticity of the sample piece.

In operation of the above constructed analyzer, firstly the sine wave signal outputted from the function generator is converted into the corresponding sine wave stress by the stress applier and is then applied to the sample piece or test piece. The stress applied to the test piece induces a strain in the test piece according to the viscoelastic characteristics thereof. The strain of the test piece is detected by the detector. The analog digital converter is operated to convert both the stress signal from the stress applier and the strain signal from the strain detector into corresponding digital values, which are then stored in the memory in a given format. The data stored in the memory is retrieved by the processor which carries out the following computation to output a measured value of the dynamic viscoelasticity of the test piece. The processor carries out Fourier transform of the digital values as follows:

$$a=\phi F(\omega t)\cdot\cos(\omega t)\, d(\omega t)$$

$$b=\phi F(\omega t)\cdot\sin(\omega t)\, d(\omega t)$$

$$A=\phi X(\omega t)\cdot\cos(\omega t)\, d(\omega t)$$

$$B=\phi X(\omega t)\cdot\sin(\omega t)\, d(\omega t)$$

where F denotes a digital value indicative of the stress generated by the stress generator, X denotes a digital value representative of the strain detected by the strain detector, $\omega$ denotes the frequency of the sine wave signal, t denotes time, and $\phi$ denotes one cycle integral.

Then, the processor carries out the following calculation:

$$M^*(\omega) = \frac{Aa + Bb + i(Ab - Ba)}{\alpha\,(A^2 + B^2)}$$

where $M^*(\omega)$ denotes a complex modulus of elasticity, $\alpha$ denotes a constant dependent on the shape of the test piece, and i denotes an imaginary unit.

DESCRIPTION OF THE PREFERRED EMBODIMENTS

Figure 1:
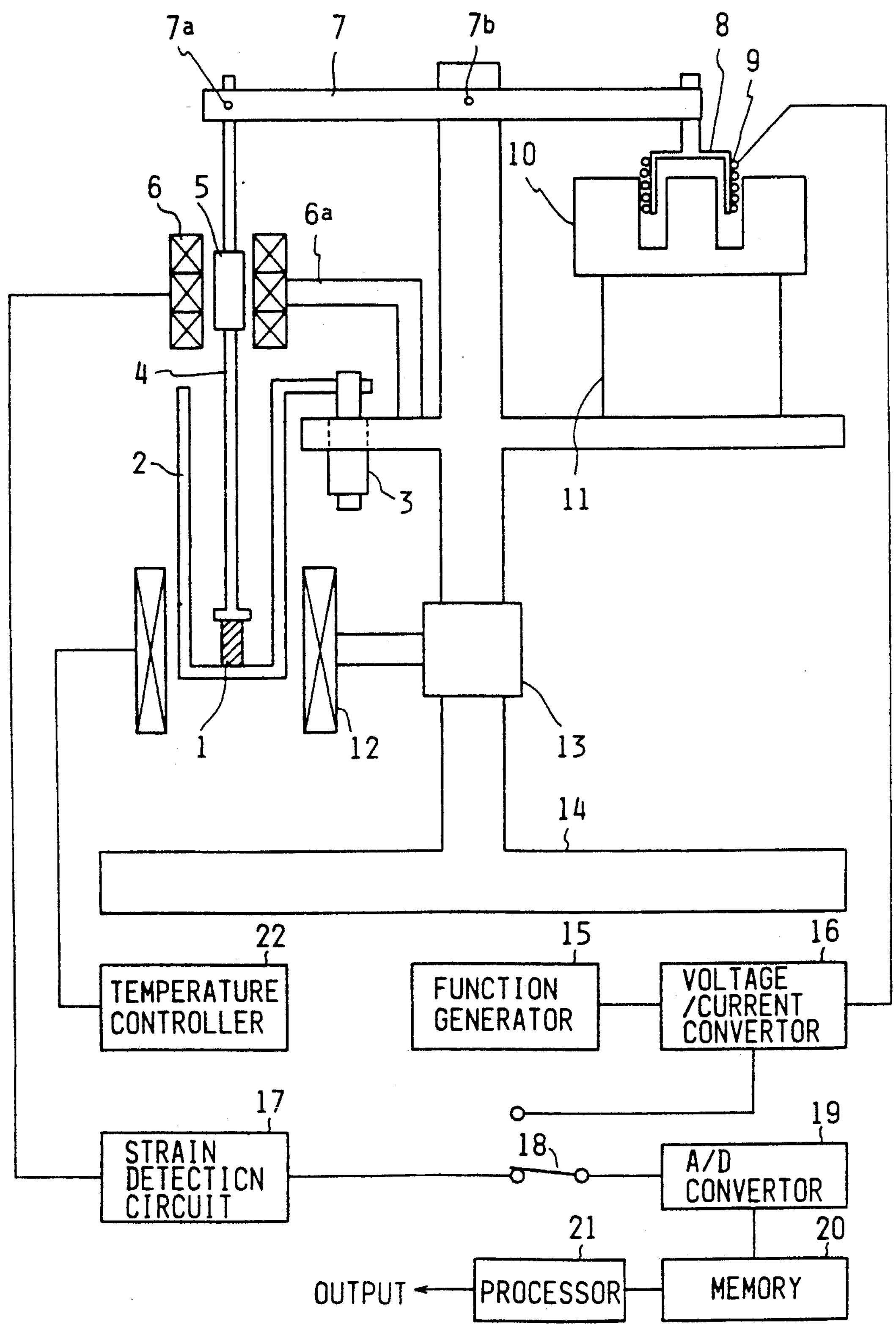
FIG. 1 is a schematic diagram showing one embodiment of the analyzer according to the invention.

Hereinafter, preferred embodiments of the invention will be described in detail with reference to the drawings. Referring to FIG. 1, a sample piece 1 is placed on the bottom of a sample holder 2. The sample holder 2 is coupled at its top end to a micrometer 3. The sample holder 2 can be displaced adjustably upwardly or downwardly by means of the micrometer 3 according to the length of sample piece 1. A rod-like probe 4 is secured to the top end of sample piece 1. The probe 4 is coupled pivotally at its upper portion to an operating point 7*a* of a lever arm 7.

Further, a core 5 is mounted on an intermediate portion of the rod-like probe 4. A differential transformer 6 is arranged to surround the core 5 to detect relative displacement of the probe 4 in the direction of its length. The differential transformer 6 is fixed via a support member 6*a* to a base frame 14 of the analyzer apparatus.

On the other hand, the arm 7 is supported pivotally at its fulcrum point 7*b* on a column of the base frame 14 to form a lever system. A coil holder 8 is coupled to an end portion of the arm 7, remote from the operating point 7*a*. A coil 9 is wound on the coil holder 8. A magnet 10 is disposed around the coil 9, and is fixed via a table 11 to a transverse part of the base frame 14. In addition, a part of the micrometer 3 is also fixed to the transverse part of the base frame 14. Further, a furnace 12 is disposed around the sample holder 2 so as to vary the temperature of sample piece 1 in a controlled manner. The furnace 12 is mounted to be slidable upwardly or downwardly, via a slider 13, along the column of the base frame 14.

A function generator 15 is provided to generate various function signals such as a sine wave signal and a DC ramp signal. A voltage current converter 16 is connected to the function generator 15 to convert the function signal into a corresponding drive current which is fed to the coil 9 to generate a stress force cooperatively with the magnet 10 according to the function signal. Therefore, the coil 9 and the magnet 10 constitute together a stress applier.

The thus generated stress force is transmitted to the sample piece 1 through the arm 7 and the probe 4 to thereby induce a strain deformation in the sample 1.

This strain deformation causes an up-and-down, or oscillating, movement of the core 5 in unison with probe 4. This movement is detected by a strain detecting circuit 17 which is connected to receive a signal from differential transformer 6 representative of the movement of core 5. Therefore, the core 5, the differential transformer 6 and the strain detecting circuit 17 constitute together a strain detector.

An analog digital, or A/D, converter 19 is connected through a switch 18 selectively to the voltage current converter 16 and to the strain detecting circuit 17 so as to convert the analog stress signal from converter 16 and the analog strain signal from circuit 17 into corresponding digital values, which are stored in a memory 20 and which are then passed to a processor 21 on demand.

In addition, a temperature controller 22 is connected to furnace 12 so as to control furnace 12 to regulate the temperature of sample piece 1.

In operation of the inventive analyzer apparatus illustrated in FIG. 1, at first the temperature controller 22 and the furnace 12 are operated to vary the temperature of the sample piece 1 according to a desired temperature profile or program. Concurrently, the function generator 15 is operated to generate a desired sine wave signal for use in measurement of dynamic viscoelasticity. Alternatively, the function generator 15 can be operated to generate a DC signal in case it is desired to measure thermal expansion ratio.

According to the wave signal generated by the function generator 15, the stress applier composed of voltage current converter 16, coil 9, magnet 10, coil holder 8, arm 7 and probe 4 operates to apply a stress to the sample piece 1 to induce a strain in the sample piece This strain is detected by the strain detector composed of the probe 4, core 5, differential transformer 6, and strain detecting circuit 7.

A/D converter 19 is employed selectively and alternatively by operation of switch 18 at a given timing, which is at a higher rate than the frequency of the sine wave produced by generator 15, to convert the analog signals representative of the stress generated by the stress applier and representative of the strain detected by the strain detector into corresponding digital signals or digital values, which are stored in the memory 20 according to a predetermined data format.

In the measurement of dynamic viscoelasticity, the processor 21 operates to retrieve the stress and strain digital values stored in the memory 20 to carry out the following digital Fourier transform computations:

$$a = \frac{1}{\pi}\int_0^{2\pi} f(\omega T)\cdot\cos(\omega t)d(\omega t) = \frac{2}{T}\sum_{k=0}^{T/T_s} F_k\cdot\cos\left(\frac{2\pi T_s}{T}\cdot k\right)\cdot T_s$$

$$b = \frac{1}{\pi}\int_0^{2\pi} F(\omega t)\cdot\sin(\omega t)d(\omega t) = \frac{2}{T}\sum_{k=0}^{T/T_s} F_k\cdot\sin\left(\frac{2\pi T_s}{T}\cdot k\right)\cdot T_s$$

$$A = \frac{1}{\pi}\int_0^{2\pi} X(\omega t)\cdot\cos(\omega t)d(\omega t) = \frac{2}{T}\sum_{k=0}^{T/T_s} X_k\cdot\cos\left(\frac{2\pi T_s}{T}\cdot k\right)\cdot T_s$$

-continued $$B = \frac{1}{\pi}\int_0^{2\pi} X(\omega t)\cdot\sin(\omega t)d(\omega t) = \frac{2}{T}\sum_{k=0}^{T/T_s} X_k\cdot\sin\left(\frac{2\pi T_s}{T}\cdot k\right)\cdot T_s$$

where $\pi$ denotes the ratio of the circumference to the diameter of a circle, $\omega$ denotes the frequency of the sine wave signal, T denotes a period $(2\pi/\omega)$ of the sine wave signal, $T_s$ denotes a sampling time interval of digital data, $F_k$ denotes a k-th stress digital value obtained after division of the period, $X_k$ denotes a k-th strain digital value obtained after division of the period, and t denotes time.

Further, processor 21 operates, based on the thus obtained Fourier-transformed values a, b, A and B, to calculate the complex modulus of elasticity M* of the sample piece to thereby output the results of the measurement of the dynamic viscoelasticity according to the following formula:

$$M^*(\omega) = \frac{L}{S}\left[\frac{A\cdot a + B\cdot b}{A^2 + B^2} + i\frac{A\cdot b - B\cdot a}{A^2 + B^2}\right] \quad (1)$$

where L denotes the length of the sample piece, and S denotes the cross-sectional area of the sample piece.

In addition, when changing the deformation mode of the sample piece from compression to shear or other modes, the formula (1) is generally applicable by suitably altering the coefficient L/S so as to accurately measure the complex modulus of the sample piece.

Figure 2:
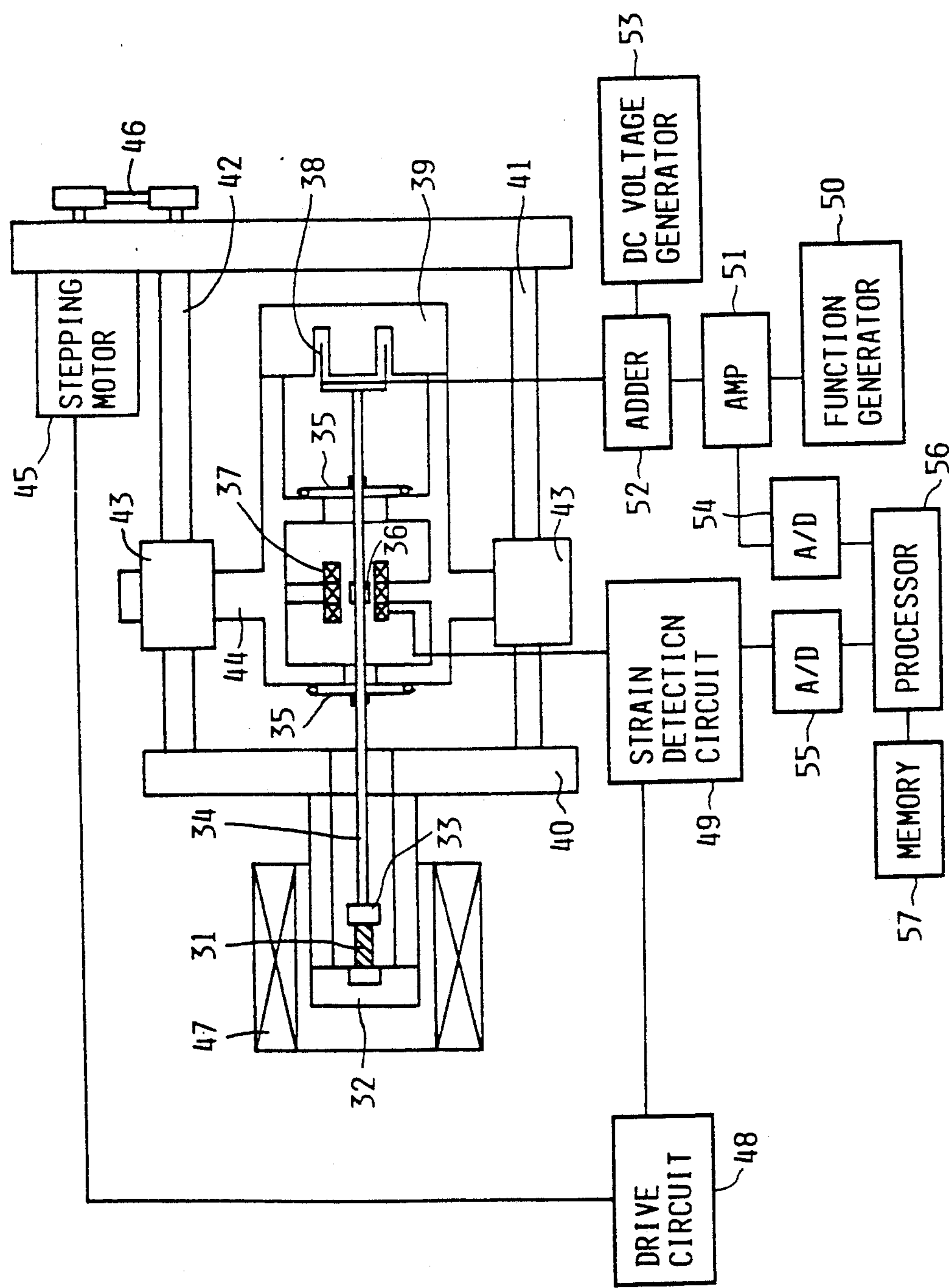
FIG. 2 is a schematic diagram showing another embodiment of the analyzer according to the invention.

Referring to FIG. 2, another embodiment will be described in detail. A sample piece 31 is held firmly at its one end by a sample holder 32 which is coupled to a base 40 of the analyzer apparatus. Another end of the sample piece 31 is held by a chuck 33 which is coupled to one end of a rod-like probe 34. The rod-like probe 34 is elastically supported via a pair of leaf springs 35 by a carriage 44 such that the probe 34 can be moved only linearly in the direction of its axis.

A core 36 is fixed to an intermediate portion of the probe 34. A differential transformer 37 is arranged around the core 36, and is fixed to the carriage 44 so as to detect a strain of the sample piece 31 in the form of a relative displacement of the core 36 such as to constitute a strain detector. A coil 38 is fixed to the other end of the probe 34, and a magnet 39 is fixed to the carriage 44 such as to surround the coil 38 to thereby constitute an electromagnetic stress applier.

Further, a furnace 47 is arranged around the sample holder 32 so as to suitably set the temperature of the sample piece 31.

A sine wave function generator 50 outputs a sine wave voltage signal, which is regulated with respect to its amplitude by an amplifier 51 and which is then fed to an adder 52. The adder 52 adds a DC voltage generated by a DC voltage generator 53 to the regulated sine wave voltage signal. The output of the adder 52 is fed to the coil 38 to generate a sine wave force superposed with a DC bias force between the coil 38 and the magnet 39. The generated force is applied through the probe 34 and the chuck 33 to the sample piece 31 to induce therein a strain. The strain generated in the sample piece 31 is transmitted in the form of the movement of the core 36 through the probe 34. This movement is detected by the differential transformer 37 to produce a strain signal which is fed to a strain detecting circuit 49.

The carriage 44 which supports thereon the stress applier and the strain detector extends between, and is connected to, a ball screw 42 and a guide rod 41 through bearings 43. A stepping motor 45 of increment type is connected to the ball screw 42 through a drive belt 46 such that the carriage 44 can be displaced in an axial direction of the ball screw 42 when the stepping motor 45 rotates the ball screw 42. Namely, the guide rod 41, ball screw 42, bearings 43, stepping motor 45 and drive belt 46 constitute together a drive mechanism for driving the carriage 44.

The stepping motor 45 is rotated in response to the output of a stepping motor device circuit 48, and the output of the drive circuit 48 is determined according to the output from the strain detecting circuit 49.

The output of the amplifier 51 is converted into a corresponding digital signal by means of a first A/D converter 54 which features a 12-bit resolution and a fast operation speed. The digital signal is fed to a processor 56 and is then stored in a memory 57. The other output of the strain detecting circuit 49 is also converted into another corresponding digital signal by means of a second A/D converter 55. This digital signal is also fed to the processor 56 and is then stored in a memory 57.

Next, the description is given for the operation of the FIG. 2 embodiment. At first, while a DC bias force is generated between the coil 38 and the magnet 39 based on the output from the DC voltage generator 53, a tension variation is induced in the sample piece 31 due to thermal expansion, softening or other causes. In order to remove or null the tension variation, the stepping motor drive circuit 48 operates to drive the stepping motor 45. When a strain output of the strain detecting circuit 49 is confined within a predetermined range, for example, $-1\mu m+1\mu m$, the sine wave function generator 50 starts to operate so as to set a measurement state or condition of the dynamic viscoelasticity. In this embodiment, the sine wave function generator 50 is tuned to produce an output at a selected one of the different frequencies of 0.01, 0.02, 0.05, 0.1, 0.2, 0.5, 1, 2, 5, 10, 50 and 100 Hz. In the measurement state for dynamic viscoelasticity, the first and second A/D converters 54 and 55 effect A/D conversion at every operating interval of 10μs. The processor 56 retrieves the digital value from the A/D converters 54 and 55 every sampling interval of, for example, 1/1000 f to store the retrieved digital value or data in the memory 57, where f(Hz) denotes the output frequency of the sine wave function generator 50. Accordingly, 1000 items of sample data are retrieved or read within one period $T=1/f$ of the sine wave signal. When completing the reading of the set of data for one period of the given sine wave signal, the measurement of dynamic viscoelasticity is temporarily suspended. Then, the stepping motor 45 is controlled again in the above described manner. Thereafter, the next measurement is restarted, and this cycle is carried out repeatedly. During the course of he operation, the furnace 47 is subjected to a temperature control in a conventional manner to regulate or set the temperature of the sample piece 31.

Next, a detailed description is given for the computation executed in the processor 56. $F_k$ and $X_k$ (k=1, 2, . . . ) denote, respectively, stress data and strain data which are sampled from the outputs of the first and second A/D converters 54 and 55 and which are stored in the memory 57 through the processor 56. At first, the processor 56 stores 4000 items of data in the memory 57 during four consecutive periods (k=1–4000). Each data item $F_k$ and $X_k$ is subjected to a smoothing operation in order to remove frequency components lower than the sine wave frequency f(Hz) to eliminate measuring error of the dynamic viscoelasticity, according to the following relations:

$$F_k = F_k - \frac{1}{1000}\sum_{n=k-500}^{k+499} F_n \qquad (k = 501\sim3501)$$

$$X_k = X_k - \frac{1}{1000}\sum_{n=k-500}^{k+499} X_n \qquad (k = 501\sim3501)$$

Next, the first half of the series data is eliminated to remove an error which would be caused by transient response at the start of the measurement. The remaining half of the series data are subjected to the following Fourier transform operation:

$$a = \frac{2}{1000}\sum_{k=2001}^{3000} F_k \cos\left[\frac{2\pi k}{1000}\right]$$

$$b = \frac{2}{1000}\sum_{k=2001}^{3000} F_k \sin\left[\frac{2\pi k}{1000}\right]$$

$$A = \frac{2}{1000}\sum_{k=2001}^{3000} X_k \cos\left[\frac{2\pi k}{1000}\right]$$

$$B = \frac{2}{1000}\sum_{k=2001}^{3000} X_k \sin\left[\frac{2\pi k}{1000}\right]$$

The processor 56 further executes computations according to the before-described formula 1 based on the Fourier-transformed values a, b, A and B to determine an elastic modulus of the sample piece.

Figure 3:
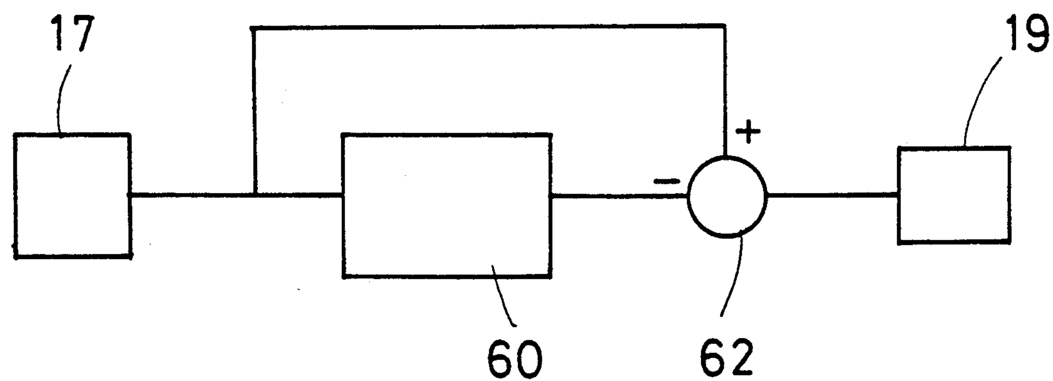
FIG. 3 is a diagram illustrating a modified portion of the embodiment of FIG. 1.

Lastly, a modification of the FIG. 1 embodiment is described with reference to FIG. 3. A filter 60 is connected to the strain detecting circuit 17 for filtering the strain signal on the basis of the period of the sine wave signal, i.e the strain signal component which varies with the sine wave signal. A subtracter 62 is connected to the output of strain detecting circuit 17 and to the output of filter 60 for carrying out a subtraction operation between the strain signal and the filtered strain signal. The A/D converter 19 converts analog outputs from the stress applier and from subtracter 62. The filter and the subtracter interposed between the strain detecting circuit 17 and the A/D converter 19 function to effect a smoothing operation in a manner similar to the FIG. 2 embodiment.

This application relates to subject matter disclosed in Japanese Application number 2-272818, filed on Oct. 11, 1990, the disclosure of which is incorporated herein by reference.

While the description above refers to particular embodiments of the present invention, it will be understood that many modifications may be made without departing from the spirit thereof. The accompanying claims are intended to cover such modifications as would fall within the true slope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A thermomechanical analyzer comprising:

a function generator for generating an analog sine wave signal;

a stress applier connected to said functioning generator for applying a sine wave stress to a sample piece according to the sine wave signal;

strain detecting means operatively connected for detecting a strain induced in the sample piece by the stress applier and for producing an analog output signal representing the strain induced in this sample piece;

an analog-to-digital converter connected to said function generator and said strain detecting means for converting the analog sine wave signal and the analog output signal procured by said strain detecting means into corresponding digital values;

a memory connected to said converter for storing the digital values;

a processor connected to receive stored digital values from said memory for carrying out fourier transform of the stored digital values to produce a representation of the dynamic viscoelasticity of the sample piece;

and adjusting means for causing the digital values corresponding to the output signal produced by said strain detecting means to represent substantially only frequency components of the output signal produced by said strain detecting means at frequencies not less than the frequency of the analog sine wave signal.

2. A thermomechanical analyzer as defined in claim 1 wherein said strain detecting mean comprises:

a detector for producing a signal directly proportional to the strain reinduced in the sample piece; and said adjusting means are incorporated in said strain detecting means and comprise;

a filter connected to said detector for filtering the signal proportional to the strain induced in the sample piece as a function of the period of the sine wave signal; and a subtraction member connected to said detector and said filter for carrying out a subtraction operation between the signal directly proportional to strain and the filtered strain signal in order to produce the analog output signal representing the strain induced in the sample piece.

* * * * *